(12) United States Patent
Thomas et al.

(10) Patent No.: US 8,492,103 B2
(45) Date of Patent: Jul. 23, 2013

(54) DIAGNOSIS AND TREATMENT OF EHRLICHIOSIS

(75) Inventors: Sunil Thomas, Dickinson, TX (US); David H. Walker, Galveston, TX (US)

(73) Assignee: The Board of Regents of the University of Texas System, Austin, TX (US)

( * ) Notice: Subject to any disclaimer, the term of this patent is extended or adjusted under 35 U.S.C. 154(b) by 0 days.

(21) Appl. No.: 13/362,765

(22) Filed: Jan. 31, 2012

(65) Prior Publication Data

US 2012/0219972 A1 Aug. 30, 2012

Related U.S. Application Data

(60) Provisional application No. 61/462,277, filed on Jan. 31, 2011.

(51) Int. Cl.
| | |
|---|---|
| *A61K 39/02* | (2006.01) |
| *A61K 39/00* | (2006.01) |
| *G01N 33/53* | (2006.01) |
| *G01N 33/554* | (2006.01) |
| *C12Q 1/00* | (2006.01) |
| *C12Q 1/68* | (2006.01) |

(52) U.S. Cl.
USPC .......... 435/7.1; 424/184.1; 424/190.1; 435/4; 435/6.15; 435/7.2; 435/7.32

(58) Field of Classification Search
None
See application file for complete search history.

(56) References Cited

U.S. PATENT DOCUMENTS 7,309,583 B2 * 12/2007 Walker et al. ............... 435/69.1
7,824,692 B2 * 11/2010 Walker et al. .............. 424/234.1
2004/0265334 A1 * 12/2004 Rikihisa et al. ............ 424/190.1

FOREIGN PATENT DOCUMENTS

WO   WO 2011125015   * 10/2011

OTHER PUBLICATIONS

Uniprot accession # Q5W8Z0 Dec. 7, 2004.*
Uniprot accession # Q5W8Z3 Dec. 7, 2004.*

* cited by examiner

*Primary Examiner* — Oluwatosin Ogunbiyi

(57) ABSTRACT

The present invention provides an isolated *Ehrlichia* peptide and therapeutic and diagnostic uses therefor.

15 Claims, 8 Drawing Sheets

DIAGNOSIS AND TREATMENT OF EHRLICHIOSIS

This application claims priority to U.S. Provisional Patent Application No. 61/462,277 filed Jan. 31, 2011, which is incorporated herein by reference in its entirety.

STATEMENT REGARDING FEDERALLY FUNDED RESEARCH

This invention was made with government support under AI31431 awarded by the National Institutes of Health. The government has certain rights in the invention.

REFERENCE TO SEQUENCE LISTING

A sequence listing required by 37 CFR 1.821-1.825 is being submitted electronically with this application. The sequence listing is incorporated herein by reference.

BACKGROUND

I. Field of Invention

The present invention relates generally to the fields of immunology, microbiology, bacteriology, and molecular biology. More specifically, the present invention relates to compositions and methods for *Ehrlichia* diagnostics and therapeutics.

II. Background

The term ehrlichiosis has been broadly applied to a variety of diseases of humans and animals caused by pathogens classified in the genus *Ehrlichia*. *Ehrlichia chaffeensis* causes human monocytic ehrlichiosis (HME). Ehrlichiosis is transmitted by the bite of infected ticks, including the lone star tick. HME was first reported in 1987. The clinical symptoms of HME include fever, headache, malaise, myalgia, rash, lymphadenopathy, and nausea (Rikihisa, 1999). HME can be fatal to the immune compromised and elderly. White-tailed deer are presumed to be the reservoir hosts of *E. chaffeensis* (Dawson et al., 1994; Lockhart et al., 1997).

Illness due to ehrlichiosis can be so mild that no medical care is sought or the illness can be severe and sometimes fatal. Symptoms are generally non-specific and other diagnoses may be considered. Because the laboratory tests that detect ehrlichiosis are often not positive in the first week of illness, physicians base early patient treatment decisions on the signs and symptoms, as well as the patient's history. The physician also looks at specific blood tests to help determine the likelihood of ehrlichiosis. Clues such as a low platelet count (thrombocytopenia), low serum sodium levels (hyponatremia), abnormal white blood cell counts (elevated or decreased), or elevated liver enzyme levels are often helpful predictors.

Serologic assays are the most frequently used methods for confirming cases of ehrlichiosis. The indirect immunofluorescence assay (IFA) is generally considered the reference standard in ehrlichiosis serology. Other assays include ELISA, latex agglutination, and dot immunoassays. Serologic tests can be used to detect either IgG or IgM antibodies. Blood samples taken early (acute) and late (convalescent) in the disease are the preferred specimens for evaluation. Most patients demonstrate increased IgM titers by the end of the first week of illness, but IgM assays may be falsely elevated due to other bacterial infections. IgG antibodies are considered more accurate for the ehrlichiosis, but detectable levels of IgG antibody generally do not appear until 7-10 days after the onset of illness. It is important to consider the amount of time it takes for antibodies to appear when ordering laboratory tests, especially because most patients visit their physician relatively early in the course of the illness, before diagnostic antibody levels may be present. The value of testing two sequential serum or plasma samples together to show a rising antibody level is important in confirming acute infection with ehrlichiosis. Because antibody titers may persist in some individuals for years after the original exposure, only demonstration of recent changes in titers between paired specimens can be considered reliable confirmation of an acute infection.

The most rapid and specific diagnostic assays for ehrlichiosis rely on molecular methods like PCR that can detect DNA present in a whole blood or tissue sample. PCR on whole blood specimens taken early during illness have been shown to be a very effective tool to diagnose ehrlichiosis. Immunostaining procedures can also be performed on formalin-fixed tissue samples. Ideally, whole blood or skin biopsy specimens used for diagnosis should be taken before or within the first 48 hours after doxycycline treatment is started; after antibiotic therapy has been started, it becomes more difficult to detect the organisms by these methods.

Canine ehrlichiosis is a disease of dogs and wild canids (e.g., wolves) and is found worldwide. Canine ehrlichiosis is also known by other names such as "tracker dog disease", "tropical canine pancytopenia", "canine hemorrhagic fever", and "canine typhus". Canine monocytic ehrlichiosis (CME) is an important tick-borne disease of dogs worldwide that is caused primarily by the obligatory intracellular organism *Ehrlichia canis* (Neer et al., 2002). *E. chaffeensis* can also infect dogs and several wild animals (Dawson et al., 1996) (Table 1). *E. canis* causes canine monocytic ehrlichiosis and was first recognized in Algeria in 1935 (Buhles et al., 1974). Wild and domestic dogs with chronic infection serve as reservoir hosts. During the acute phase of infection, the clinical signs include fever, anorexia, and lymphadenopathy, and, in the chronic phase of infection, the dogs may show emaciation, hemorrhage, and peripheral edema (Buhles et al., 1974).

Two blood tests that detect the dog's antibodies to *Ehrlichia* are available. One is called the indirect immunofluorescent antibody (IFA) test, and the other is ELISA test. A veterinarian cannot rely solely on these tests to make a diagnosis. The antibodies may not be detected in the early phase of the disease, since it takes some time for the body to make them. Also, if a dog is extremely ill, it may not be able to produce enough antibodies to be accurately detected. A positive test demonstrates that the dog has been exposed to *Ehrlichia*, but not that it necessarily is currently infected. In the acute stage of the disease, the antibody level will rise significantly. Often two tests will be done 2 weeks apart and the results compared. Dogs with an active infection will show a significant rise in the amount of antibody present. The antibodies can last for one or more years after the infection, but they do not make the dog immune to ehrlichiosis—the dog can be reinfected.

Techniques using PCR test for the presence of the organism itself, not antibodies to it. Unfortunately, it does not distinguish between live and dead organisms. For this reason, it is generally recommended to perform the PCR along with one of the antibody tests to make a diagnosis. There is no vaccine for ehrlichiosis currently. Thus, new methods and compositions are needed to diagnose and treat ehrlichiosis.

SUMMARY

The inventors have designed peptides to the epitopes of *Ehrlichia muris* outer membrane P28-19 (OMP-1/P28) and *Ehrlichia* Heat shock protein 60 (Hsp60/GroEL, see U.S. Patent Publication 20110117130) antigenic proteins. Both P28-19 and *Ehrlichia* Hsp60 peptides reacted with polyclonal antibodies against *E. canis* and *E. chaffeensis* and could be used as a diagnostic tool for ehrlichiosis. In addition, the inventors demonstrate that vaccination with *Ehrlichia* P28-19 and Hsp60 peptides and later challenged with *E. muris* protected against ehrlichiosis.

*E. muris* P28-19 protein has the following sequence (SEQ ID NO: 1)

```
  1 mnckrifiks alislisflp gisfsdpiqd snvsgnfyis gkympsashf gvfsakeekn
 61 ataktfglkq dwdgaaisnt stdvftisny sfkyennpfl qfagaigysm ggpriefevs
121 yetfdvknqq nnykndahry yalsqdttia qnkfvvlkne gladisfmln acydvttegi
181 pfspyicagi gtdlvsmfea tspkisyqgk lglsysispe tsvfvgghfh kvvgnefkdv
241 paivpsgstl agnhfaivtl nvchfgielg grfaf
```

Peptides of P28-19 include akeeknataktfglkq (P28-19-1, SEQ ID NO:2), sfkyennpflgfagaigysm (P28-19-2, SEQ ID NO:3), and yetfdvknqgnnykndahryyals (P28-19-3, SEQ ID NO:4).

*Ehrlichia* Hsp60 protein has the following sequence (SEQ ID NO: 5)

```
  1 manvvvtgeq ldksirevvr iledavgcta gpkgltvais ksygapeitk dgykviksik
 61 pedplalaia niitqsasqc ndkvgdgttt csiltakvie evskakaaga divcikegvl
121 kakeavleal msmkrevlse eeiaqvatis angdknigsk iaqcvqevgk dgvitveesk
181 qfkeldvekt dgmqfdrqyl spyfvtnsek mlvefenpyi lltekklnii qpilpilenv
241 arsgrpllii aedvegeals tlvlnklrgg lhvaavkapg fgdrrkdmlg diailtgakh
301 visddlaikm edltlaelgt akniritkdt ttiigsvdns stnvqsrinq ikmqieasts
361 dydkeklrer laklsggvav lkvggsseve vkerkdrved alhatraave
```

Peptides of the Hsp60 protein include ygapeitkdgykviksikped (SEQ ID NO:6), skgfkeldvektdgmqfdrgyl (SEQ ID NO:7), and sevevkerkdrvedalhatraave (SEQ ID NO:8).

The term ehrlichiosis has been broadly applied to a variety of human and animal diseases caused by pathogens classified in the genus *Ehrlichia*. The obligatory intracellular bacterium *Ehrlichia chaffeensis*, which resides in mononuclear phagocytes, is the causative agent of human monocytotropic ehrlichiosis, whereas *Ehrlichia canis* causes ehrlichiosis in dogs.

Certain embodiments are directed to an isolated peptide having a sequence at least 80, 85, 90, 95, 98, or 100% homologous or identical to the amino acid sequence of SEQ ID NOS: 2, 3, 4, 6, 7, or 8. In certain aspects, the peptide is 10, 11, 12, 13, 14, 15, 16, 17, 18, 19, 20, 21, 22, 23, 24, 25 or more consecutive amino acids of an *Ehrlichia* protein in length. In certain aspects, the composition further comprises a carrier. In a further aspect, the peptide is coupled to a substrate or surface, e.g, bead, ELISA plate, nitrocellulose, plastic, glass, etc. In still a further aspect, the peptide is coupled to a label.

"Substantially pure" or "isolated" refers to a peptide or nucleic acid that is not part of a protein, nucleic acid, or milieu in which it naturally occurs, by virtue of separation, or partial or total purification from some or all of the molecules or context of its natural state or from its natural milieu.

The identity between two sequences is a direct function of the number of matching or identical positions. When a subunit position in both of the two sequences is occupied by the same monomeric subunit, e.g., if a given position is occupied by an adenine in each of two DNA molecules, then they are identical at that position. For example, if 7 positions in a sequence 10 nucleotides in length are identical to the corresponding positions in a second 10-nucleotide sequence, then the two sequences have 70% sequence identity. Sequence identity is typically measured using sequence analysis software (e.g., Sequence Analysis Software Package of the Genetics Computer Group, University of Wisconsin Biotechnology Center, 1710 University Avenue, Madison, Wis. 53705).

A further aspect is directed to a vaccine against *Ehrlichia* comprising a peptide having a sequence at least 80, 85, 90, 95, 98, or 100% identical to the amino acid sequence of SEQ ID NOS: 2, 3, 4, 6, 7, or 8. In certain aspects the peptide is 10, 11, 12, 13, 14, 15, 16, 17, 18, 19, 20, 21, 22, 23, 24, 25 or more amino acids of an *Ehrlichia* protein in length.

The instant invention is also directed to an antibody or antibody fragment that binds a peptide having a sequence at least 80, 85, 90, 95, 98, or 100% identical to the amino acid sequence of SEQ ID NOS: 2, 3, 4, 6, 7, or 8. In certain aspects, the peptide is 10, 11, 12, 13, 14, 15, 16, 17, 18, 19, 20, 21, 22, 23, 24, 25 or more amino acids of an *Ehrlichia* protein in length.

Certain aspects are directed to a method of determining whether a subject is infected with *Ehrlichia*, comprising the steps of: contacting a sample from a subject with an antibody or peptide described herein; and detecting a resulting antibody or peptide reaction or complex, wherein a positive reaction indicates the subject is infected with *Ehrlichia*.

Still further aspects are directed to a diagnostic or a serodiagnostic kit for detecting *Ehrlichia* or determining whether a subject is infected with *Ehrlichia*, said kit comprising an antibody or peptide described herein. In certain aspects the antibody or peptide is linked to a detectable label or reporter molecule. The kit can also contain a buffer and/or reagents for detection of an immunocomplex, detectable label, and/or reporter molecule. In other aspects, peptides of the invention can be comprised in *Ehrlichia* detection kits to determine the presence or absence of *Ehrlichia* in a sample, be it biological or environmental.

As used herein, the term "antigen" is a molecule capable of being bound by an antibody or T-cell receptor. An antigen is additionally capable of inducing a humoral immune response and/or cellular immune response leading to the production of B- and/or T-lymphocytes. The structural aspect of an antigen, e.g., three dimensional conformation or modification (e.g., phosphorylation), that gives rise to a biological response is referred to herein as an "antigenic determinant" or "epitope." B-lymphocytes respond to foreign antigenic determinants via antibody production, whereas T-lymphocytes are the mediator of cellular immunity. Thus, antigenic determinants or epitopes are those parts of an antigen that are recognized by antibodies, or in the context of an MHC, by T-cell receptors. An antigenic determinant need not be a contiguous sequence or segment of protein and may include various sequences that are not immediately adjacent to one another. In certain aspects, Tau oligomers are utilized as antigens.

The term "immunological" or "immune" or "immunogenic" response refers to the development of a humoral (antibody mediated) and/or a cellular (mediated by antigen-specific T cells or their secretion products) response directed against an antigen in a vertebrate individual. Such a response can be an active response induced by administration of an immunogen (e.g., an antigenic peptide) or a passive response induced by administration of an antibody.

As used herein the terms "specific to" or "specific for" a target sequence, in relation to an antibody, relate to an antibody or antibody fragment that binds an antigen, under conditions used in given circumstances (e.g., temperature, salt concentration, etc.), but does not significantly bind to other antigens or polypeptides under those circumstances that are not target antigens.

Other embodiments of the invention are discussed throughout this application. Any embodiment discussed with respect to one aspect of the invention applies to other aspects of the invention as well and vice versa. Each embodiment described herein is understood to be embodiments of the invention that are applicable to all aspects of the invention. It is contemplated that any embodiment discussed herein can be implemented with respect to any method or composition of the invention, and vice versa. Furthermore, compositions and kits of the invention can be used to achieve methods of the invention.

The use of the word "a" or "an" when used in conjunction with the term "comprising" in the claims and/or the specification may mean "one," but it is also consistent with the meaning of "one or more," "at least one," and "one or more than one."

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DESCRIPTION OF THE DRAWINGS

The following drawings form part of the present specification and are included to further demonstrate certain aspects of the present invention. The invention may be better understood by reference to one or more of these drawings in combination with the detailed description of the specification embodiments presented herein.

DESCRIPTION

Figure 1:
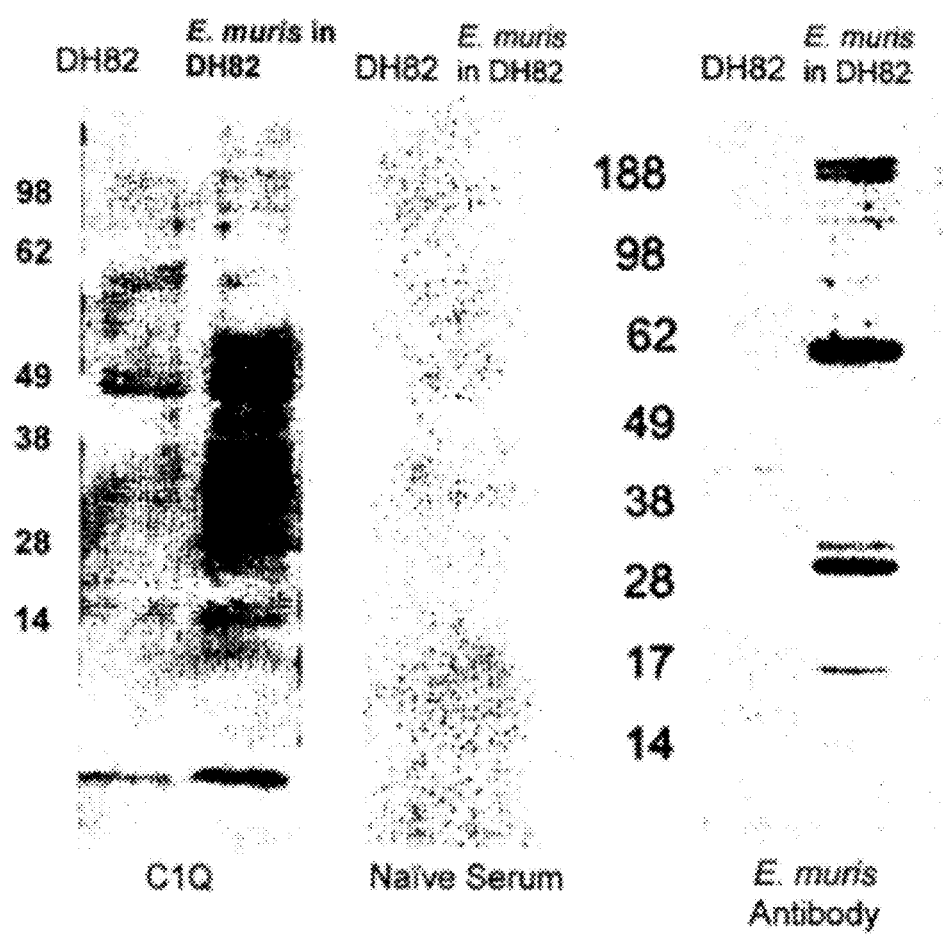
FIG. 1 shows that the complement protein C1Q interacted through the antibodies with $Ehrlichia$ antigens-P100, P50, P45, P30, P28, and P14. The $E.$ $muris$ antibody interacts with $Ehrlichia$ antigens-P180, P150, Hsp60, P28, P17 and P14.

Ehrlichioses are tick-borne diseases of veterinary medical importance and are also important emerging infectious diseases in humans. P28s are encoded by multigene families with ORFs tandemly arranged with intergenic spaces of variable lengths (Crocquet-Valdes et al., 2005). The P28 gene family represents a series of 21 homologous genes (20 to 83% amino acid identity) that are arranged in tandem in the *E. chaffeensis* genome (Gusa et al., 2001).

The P28 protein is the major antigenic protein of *Ehrlichia* as determined by Western blotting (Thomas et al., 2009) and by eastern blotting it was demonstrated that P28 is post translationally modified. As P28 is the major antigenic protein, it was contemplated by the inventors that P28 could be used as a diagnostic or vaccine.

The inventors contemplated that peptides will provide better diagnostic and vaccine candidates compared to the whole recombinant proteins. Three peptides of the P28-19 antigenic protein were designed of which the P28-19-1 was found to be highly sensitive in detection of *Ehrlichia*. The peptide was also very sensitive in diagnosis of *Ehrlichia* compared to the whole recombinant P28-19.

As the sequence of this peptide is highly conserved in *Ehrlichia* it could be used in diagnosis of any species of *Ehrlichia*. Diagnosis of antibodies of *Ehrlichia* from different species by the peptides demonstrated that they could be used in diagnosis of *Ehrlichia*. The peptides did not cross-react with the antibody of different species of *Rickettsia* or *Orientia* demonstrating that they are highly specific for only *Ehrlichia*.

Certain embodiments are directed to an isolated *Ehrlichia* peptide having a sequence at least 80, 85, 90, 95, 98, or 100% identical to the amino acid sequence of SEQ ID NOS: 2, 3, 4, 6, 7, or 8. Two sequences are "substantially homologous" when at least about 75% (preferably at least about 80%, 85%, 90%, 95%, 98%, or 100%) of the residues match or are identical over the defined length of the sequences. Publicly available software can be used to compare sequences and identify those that are substantially homologous.

In one aspect, the peptide may be dispersed in a pharmaceutically acceptable composition. The phrase "pharmaceutically acceptable" refers to molecular entities and compositions that do not produce an allergic or similar untoward reaction when administered to a human. The preparation of an aqueous composition that contains a protein as an active ingredient is well understood in the art. Typically, such compositions are prepared as injectables, either as liquid solutions or suspensions; solid forms suitable for solution in, or suspension in, liquid prior to injection can also be prepared. The preparation can also be emulsified.

A protein may be formulated into a composition in a neutral or salt form. Pharmaceutically acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Upon formulation, solutions will be administered in a manner compatible with the dosage formulation and in such amount as is therapeutically effective. The formulations are easily administered in a variety of dosage forms such as injectable solutions.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media that can be employed will be known to those of skill in the art in light of the present disclosure. For example, one dosage could be dissolved in 1 ml of isotonic NaCl solution and either added to 1,000 mL of hypodermoclysis fluid or injected at the proposed site of infusion, (see for example, "Remington's Pharmaceutical Sciences" 15th Edition, pages 1,035-1,038 and 1,570-1,580). Some variation in dosage will necessarily occur depending on the condition of the subject being treated. The person responsible for administration will, in any event, determine the appropriate dose for the individual subject.

A person having ordinary skill in this art would readily be able to manipulate the peptide of SEQ ID NOS: 2, 3, 4, 6, 7, or 8 in order to derive slightly different peptides with the same functions and uses as the peptide of SEQ ID NOS: 2, 3, 4, 6, 7, or 8. Accordingly, the present invention also encompasses peptides that are at least 95% identical to the amino acid sequence of SEQ ID NOS: 2, 3, 4, 6, 7, or 8. The present invention also encompasses peptides that are at least 90% identical to the amino acid sequence of SEQ ID NOS: 2, 3, 4, 6, 7, or 8, peptides that are at least 85% identical to the amino acid sequence of SEQ ID NOS: 2, 3, 4, 6, 7, or 8 as well as peptides that are at least 80% identical to the amino acid sequence of SEQ ID NOS: 2, 3, 4, 6, 7, or 8.

Peptides may further comprise a label. In one aspect of this embodiment of the present invention, the peptide is chemically synthesized. In one aspect of this embodiment, the peptide is produced in a host cell. The peptide may further comprise a carrier. Further, the peptide may be conjugated to the carrier. For example, the protein and carrier may be conjugated by glutaraldehyde, m-maleimidobenzoyl-N-hydroxysuccinimide ester, carbo-diimide or bis-biazotized benzidine. Representative examples of useful carriers include keyhole limpet hemocyanin (KLH), human serum albumin, a lymphokine, or an adjuvant. Representative examples of useful adjuvants include IL2, IL4, IL8, BCG, Detox, RIBI, ISCOMS, or aluminum hydroxide.

In another embodiment, the present invention provides a vaccine against *Ehrlichia* comprising a peptide at least 80, 85, 90, 95, 98, or 100% identical to the amino acid sequence of SEQ ID NOS: 2, 3, 4, 6, 7, or 8. As is well known in the art, a given polypeptide may vary in its immunogenicity. In certain aspects, an immunogen may be coupled (e.g., a peptide of the present invention) with a carrier. Exemplary and preferred carriers are keyhole limpet hemocyanin (KLH) and human serum albumin. Other carriers may include a variety of lymphokines and adjuvants such as IL2, IL4, IL8 and others. Means for conjugating a peptide to a carrier protein are well known in the art and include glutaraldehyde, m-maleimido-benzoyl-N-hydroxysuccinimide ester, carbo-diimide and bis-biazotized benzidine. It is also understood that the peptide may be conjugated to a protein by genetic engineering techniques that are well known in the art, such as peptide fusion.

As is also well known in the art, immunogenicity to a particular immunogen can be enhanced by the use of non-specific stimulators of the immune response known as adjuvants. Exemplary and preferred adjuvants include complete BCG, Detox, RIBI (Immunochem Research Inc.), ISCOMS and aluminum hydroxide adjuvant (Superphos, Biosector).

In another embodiment, the present invention provides an antibody that is directed against, i.e., that specifically binds to, a peptide at least 80, 85, 90, 95, 98, or 100% identical to the amino acid sequence of SEQ ID NOS: 2, 3, 4, 6, 7, or 8

In another embodiment, the present invention provides a method of determining whether a subject is infected with *Ehrlichia*, comprising the steps of: contacting a sample from a subject with an antibody or peptide described herein; and detecting a resulting antibody/peptide reaction, wherein a positive reaction indicates the subject is infected with *Ehrlichia*. The subject can be a dog, a human, or a ruminant. In one aspect of this embodiment of the present invention, the sample is a biological sample, such as a serum. Samples also include biological material derived from a tick or other insect. *Ehrlichia* includes, but is not limited to *Ehrlichia chaffeensis*, *Ehrlichia muris*, and *Ehrlichia canis*.

In another embodiment, the present invention provides a diagnostic or serodiagnostic kit for determining whether a sample or a subject is infected with *Ehrlichia*, said kit comprising one or more of (a) an antibody or peptide described herein, the antibody or peptide being directly or indirectly linked to a label or a surface; (b) a buffer; and/or (c) a reagent for detection of the label. Representative labels include those selected from the group consisting of luciferase, horseradish peroxidase, β-galactosidase and fluorescent labels.

Labels include, but are not limited to moieties that are directly or indirectly detectable such as radioactive elements, enzymes, fluorescent molecules or chemicals, and others. A number of fluorescent materials are known and can be utilized as labels. These include, for example, fluorescein, rhodamine, auramine, Texas Red, AMCA blue and Lucifer Yellow. A particular detecting material is anti-rabbit antibody prepared in goats and conjugated with fluorescein, e.g., through an isothiocyanate.

Proteins (e.g., antibodies) or peptides can also be labeled with a radioactive element or with an enzyme. The radioactive label can be detected by any of the currently available counting or detection procedures. The preferred isotope may be selected from $^3$H, $^{14}$C, $^{32}$P, $^{35}$S, $^{36}$Cl, $^{51}$Cr, $^{57}$Co, $^{58}$Co, $^{59}$Fe, $^{90}$Y, $^{125}$I, $^{131}$I, and $^{186}$Re. Enzyme labels can be detected by any of the presently utilized calorimetric, spectrophotometric, fluorospectrophotometric, amperometric or gasometric techniques. The enzyme is conjugated to the selected particle by reaction with bridging molecules such as carbodiimides, diisocyanates, glutaraldehyde and the like. Enzymes used as detectable labels include, but are not limited to peroxidase, β-glucuronidase, β-D-glucosidase, β-D-galactosidase, urease, glucose oxidase plus peroxidase and alkaline phosphatase. U.S. Pat. Nos. 3,654,090, 3,850,752, and 4,016,043 are referred to by way of example for their disclosure of alternate labeling material and methods.

By a "substantially pure protein" is meant a protein that has been separated from at least some of those components that naturally accompany it. Typically, the protein is substantially pure when it is at least 60%, by weight, free from the proteins and other naturally occurring organic molecules with which it is naturally associated in vivo. Preferably, the purity of the preparation is at least 75%, more preferably at least 90%, and most preferably at least 99%, by weight. A protein is substantially free of naturally associated components when it is separated from at least some of those contaminants that accompany it in its natural state. Thus, a protein that is chemically synthesized or produced in a cellular system different from the cell from which it naturally originates will be, by definition, substantially free from its naturally associated components. Accordingly, substantially pure proteins include eukaryotic proteins synthesized in *E. coli*, other prokaryotes, or any other organism in which they do not naturally occur.

In accordance with the present invention there may be employed conventional molecular biology, microbiology, and recombinant DNA techniques. Such techniques are explained fully in the literature. See, e.g., Maniatis, Fritsch & Sambrook, "Molecular Cloning: A Laboratory Manual (1982); "DNA Cloning: A Practical Approach," Volumes I and II (D. N. Glover ed. 1985); "Oligonucleotide Synthesis" (M. J. Gait ed. 1984); "Nucleic Acid Hybridization" [B. D. Hames & S. J. Higgins eds. (1985)]; "Transcription and Translation" [B. D. Hames & S. J. Higgins eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984).

For instance, as used herein, the term "host cell" is meant to include not only prokaryotes but also eukaryotes such as yeast, plant, and animal cells. A recombinant DNA molecule or gene that encodes a peptide as described herein, e.g., the peptide of SEQ ID NO. 2, can be used to transform a host cell using any of the techniques commonly known to those of ordinary skill in the art. Prokaryotic host cells may include *E. coli*, *S. typhimurium*, *Serratia marcescens* and *Bacillus subtilis*. Eukaryotic host cells include yeasts such as *Pichia pastoris*, mammalian cells and insect cells.

As used herein, the term "engineered" or "recombinant" cell is intended to refer to a cell into which a recombinant gene, such as a gene encoding an antigen has been introduced. Therefore, engineered cells are distinguishable from naturally occurring cells that do not contain a recombinantly introduced gene. Engineered cells are thus cells having a gene or genes introduced through the hand of man. Recombinantly introduced genes will either be in the form of a cDNA gene, a copy of a genomic gene, or will include genes positioned adjacent to a promoter not naturally associated with the particular introduced gene. In addition, the recombinant gene may be integrated into the host genome, or it may be contained in a vector, or in a bacterial genome transfected into the host cell.

An expression vector is a replicable construct in which a nucleic acid sequence encoding a polypeptide is operably linked to suitable control sequences capable of effecting expression of the polypeptide in a cell. The need for such control sequences will vary depending upon the cell selected and the transformation method chosen. Generally, control sequences include a transcriptional promoter and/or enhancer, suitable mRNA ribosomal binding sites, and sequences that control the termination of transcription and translation. Methods, which are well known to those skilled in the art, can be used to construct expression vectors containing appropriate transcriptional and translational control signals. See for example, the techniques described in Sambrook et al., 1989, Molecular Cloning: A Laboratory Manual (2nd Ed.), Cold Spring Harbor Press, N.Y. A gene and its transcription control sequences are defined as being "operably linked" if the transcription control sequences effectively control the transcription of the gene. Vectors of the invention include, but are not limited to, plasmid vectors and viral vectors. Preferred viral vectors of the invention are those derived from retroviruses, adenovirus, adeno-associated virus, SV40 virus, or herpes viruses.

III. EXAMPLES

The following examples as well as the figures are included to demonstrate preferred embodiments of the invention. It should be appreciated by those of skill in the art that the techniques disclosed in the examples or figures represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Diagnostic and Therapeutic *Ehrlichia* Peptides

A. Results
Detection of Complement Binding Antigen.
To detect *Ehrlichia* antigens binding to the complement C1Q, *E. muris* lysate were run on an SDS-PAGE and the proteins blotted on to a nitrocellulose membrane. The blot was probed with mouse anti-*E. muris* antibody (1:750) followed by probing with rat anti-mouse C1Q (1:750) and anti-rat HRP (1:1000). Finally the blots were incubated with chemiluminescence substrate (Millipore, MA) and the blot exposed to a film (Kodak).

Detection of *Ehrlichia* Antibody in Sera of Mice Infected with *E. Muris* Using Different P28 Peptides.

To detect sensitivity of the P28 peptides (P28-1, P28-2, P28-3) or recombinant P28, peptides were coated on a NUNC Maxisorp plate (1:250), followed by incubation with *E. muris* serum. Finally, they were probed with goat anti-mouse AP (1:500) and results read on an ELISA reader after the addition of substrate.

Detection of *Ehrlichia* Antibody in Sera of Dogs Infected with *E. canis, E. chaffeensis* and *E. ewingii* Using P28 Peptide.

ELISA plates (Nunc, Maxisorp) were coated with P28-1 and incubated with sera of dogs (infected with *E. canis, E. chaffeensis* and *E. ewingii*) (1:100) (1 hour-RT) followed by incubation with goat anti-dog AP (1:1500). Results were quantitated using an ELISA reader after the addition of substrate.

Detection of *Ehrlichia* Antibody in Sera of Humans Infected with *E. chaffeensis* Using P28 Peptide.

ELISA plates (Nunc, Maxisorp) were coated with P28-1 and incubated with sera of humans (infected with E. chaffeensis) (1:100) (1 hour-RT) followed by incubation with goat anti-human AP (1:1500). Results were quantitated using an ELISA reader after the addition of substrate.

Detection of *Ehrlichia* Antibody in Sera of Mice Vaccinated with *Ehrlichia* Hsp60 and Challenged with *E. muris* Using P28 Peptide.

ELISA plates (Nunc, Maxisorp) were coated with P28-1 and incubated with sera of mice (1:100) vaccinated with *Ehrlichia* Hsp60 and challenged with *E. muris*. Following incubation with mice sera they were incubated with goat anti-mouse AP (1:500). Results were quantitated using an ELISA reader after the addition of substrate.

Determination of the Specificity of P28 Peptides.

To determine the specificity of the P28-1 peptide, they were coated with P28-1 and incubated with sera of mice (1:100) infected with *Ehrlichia* or different *Rickettsia* species. Following incubation with mice sera, they were incubated with goat anti-mouse AP (1:500). Results were quantitated using an ELISA reader after the addition of substrate.

Detection of *E. muris* by Immunofluorescence Microscopy.

P28-19-1 peptides were injected in mice (50 micrograms) (two doses, 15 days apart) and the serum collected on day 45 after the first injection. DH82 cells infected with *E. muris* were probed with the antibody (1:100 dilution), followed by incubating with goat anti-mouse FITC (1:300). Control consisted of antibody from naïve mouse (1:100) followed by incubating with goat anti-mouse FITC (1:300).

*Ehrlichia* Antibody Recognizes P28.

*E. muris* lysate was probed with *E. muris* serum from infected mice. The antibody recognized P28 protein (FIG. 1). The P28 antigen was post-translationally modified.

P28 Recognized by Complement Protein.

Though complement proteins are known to be involved in innate immunity, mediate endocytosis of intracellular bacteria and are involved in adaptive immune upregulation, the role of complement in *Ehrlichia* infection has not been demonstrated. The complement proteins effectiveness in initial defense and as stimulators of acquired immunity is determined by its ability to link itself physically to the antigens of invading microorganisms (Nielson and Leslie, 2002). The complement proteins bind to the IgG or IgM isotypes, which in turn bind to the antigenic proteins.

Studies demonstrated that *Ehrlichia* infection led to an increase in complement proteins and immunoglobulins. The antigenic protein profile of *E. muris* was found to be different when probed for the complement protein C1Q or for *E. muris* antibody alone. The complement proteins bound to the *Ehrlichia* antigens: p100, p50, p45, p30, P28 and p14 mediated through the immunoglobulins-IgM or IgG (FIG. 1). As P28 was found binding to the antibody as well as complement proteins, it was decided to use it as a probe to detect *Ehrlichia*.

Design of P28 Peptides.

The P28-19 protein sequence was used to design immunogenic peptides. When examining a protein sequence for potential antigenic epitopes; it is important to choose sequences that are hydrophilic, surface-oriented, and flexible. Most naturally occurring proteins in aqueous solutions have their hydrophilic residues on the protein surface and hydrophobic residues buried in the interior. This optimization is based on the fact that antibodies tend to bind to epitopes on the protein surface. Additionally, it has been shown that epitopes have a high degree of mobility. When designing a peptide for antibody production, the first task is to decide upon the desired location of the antibody-binding site on the protein of interest. Hydropathy plots of the amino acid sequence can be performed to determine the hydrophilicity of various regions of the protein (Kyte and Doolittle, 1982). Because hydrophilic regions are more likely to be exposed on the protein, an anti-peptide antibody to a hydrophilic sequence will be more likely to recognize the protein. Also, hydrophilic peptides dissolve more easily in aqueous solutions and are easier to work with.

Three regions of the *E. muris* P28-19 protein sequence had good hydrophilicity determined by the Lasergene software (DNAStar, WI, USA). The peptides corresponded to amino acids 55-75, 91-103, 124-145 (Table 1). The peptides showed homology to other, *Ehrlichia* species (Table 2). The peptides (underlined) were synthesized and conjugated to KLH (Biosynthesis, TX) and used as a probe to detect *Ehrlichia*.

TABLE 2

Analysis of the peptides showing homology to other *Ehrlichia* species

| Accession | Description | Max score | Total score | Query coverage | E value |
|---|---|---|---|---|---|
| Peptide 1: akeeknataktfglkqdwdga (SEQ ID NO: 2) Sequence producing significant alignments: | | | | | |
| ABD93659.1 | major outer membrane protein P28-19 [*Ehrlichia muris*] | 68.9 | 68.9 | 100% | 7e-11 |
| BAD66851.1 | major outer membrane protein P28a-1 [*Ehrlichia* sp. HF565] | 62.6 | 62.6 | 95% | 6e-09 |
| BAD66846.1 | major outer membrane protein P28a [*Ehrlichia* sp. Shizuoka-36] >dbj\|BAD66850.1\| major outer membrane protein P28a [*Ehrlichia* sp. Shizuoka-37] | 54.9 | 54.9 | 95% | 1e-06 |
| AAL12923.1 | outer membrane protein P28 [*Ehrlichia chaffeensis*] | 50.3 | 50.3 | 95% | 3e-05 |
| AAL12919.1 | outer membrane protein P28 [*Ehrlichia chaffeensis*] | 50.3 | 50.3 | 95% | 3e-05 |
| AAO12958.1 | 28 kDa outer membrane protein gene 19 [*Ehrlichia chaffeensis*] | 50.3 | 50.3 | 95% | 3e-05 |
| AAC31548.1 | outer membrane protein P28 precursor [*Ehrlichia chaffeensis*] | 50.3 | 50.3 | 95% | 3e-05 |
| YP_303546.1 | surface antigen msp4 [*Ehrlichia canis* str. Jake] >gb\|AAC68667.1\| major outer membrane protein P30 [*Ehrlichia canis*] >gb\|AAG14362.1\|P28-8 [*Ehrlichia canis*] >gb\|AAZ68948.1\|Surface antigen msp4 [*Ehrlichia canis* str. Jake] | 50.3 | 50.3 | 95% | 3e-05 |
| AAC31546.1 | outer membrane protein P28 precursor [*Ehrlichia chaffeensis*] | 46.9 | 46.9 | 95% | 3e-04 |
| AAL12921.1 | outer membrane protein P28 [*Ehrlichia chaffeensis*] | 46.9 | 46.9 | 95% | 3e-04 |
| AAO12934.1 | 28 kDa outer membrane protein gene 15 [*Ehrlichia chaffeensis*] | 42.2 | 42.2 | 95% | 0.008 |
| AAO12961.1 | 28 kDa outer membrane protein gene 15 [*Ehrlichia chaffeensis*] >gb\|AAO12967.1\|AF479840 3 28 kDa outer membrane protein gene 15 [*Ehrlichia chaffeensis*] | 42.2 | 42.2 | 95% | 0.008 |
| AAO12963.1 | 28 kDa outer membrane protein gene 17 [*Ehrlichia chaffeensis*] >gb\|AAO12969.1\|AF479840 5 28 kDa outer membrane protein gene 17 [*Ehrlichia chaffeensis*] | 42.2 | 42.2 | 95% | 0.008 |
| ABL74273.1 | P28 [*Ehrlichia canis*] | 41.8 | 41.8 | 95% | 0.011 |
| AAK28699.1 | major outer membrane protein P30-2 [*Ehrlichia canis*] | 41.8 | 41.8 | 95% | 0.011 |
| AAG14361.1 | P28-6 [*Ehrlichia canis*] | 41.8 | 41.8 | 95% | 0.011 |
| YP_303544.1 | surface antigen msp4 [*Ehrlichia canis* str. Jake] >gb\|AAZ68946.1\|Surface antigen msp4 [*Ehrlichia canis* str. Jake] | 41.8 | 41.8 | 95% | 0.011 |
| BAD66858.1 | major outer membrane protein P28b-2 [*Ehrlichia muris*] | 40.1 | 40.1 | 95% | 0.034 |
| BAD66857.1 | major outer membrane protein P28b-1 [*Ehrlichia muris*] | 40.1 | 40.1 | 95% | 0.034 |
| ABD93657.1 | major outer membrane protein P28-17 [*Ehrlichia muris*] | 39.2 | 39.2 | 95% | 0.062 |
| BAD66847.1 | major outer membrane protein P28b-1 [*Ehrlichia* sp. Shizuoka-36] | 39.2 | 39.2 | 95% | 0.062 |
| BAD66859.1 | major outer membrane protein P28b-3 [*Ehrlichia muris*] | 39.2 | 39.2 | 95% | 0.062 |
| AAC64550.2 | P28-7 [*Ehrlichia canis*] | 38.8 | 38.8 | 95% | 0.083 |
| AAC68666.1 | major outer membrane protein P30-1 [*Ehrlichia canis*] | 38.8 | 38.8 | 95% | 0.083 |

TABLE 2-continued

Analysis of the peptides showing homology to other _Ehrlichia_ species

| Accession | Description | Max score | Total score | Query coverage | E value |
|---|---|---|---|---|---|
| ABO36256.1 | Omp-1-16 [_Ehrlichia ewingii_] | 35.4 | 35.4 | 100% | 0.88 |
| AAG44895.1 | 28 kDa major outer membrane protein P28 [_Ehrlichia ewingii_] >gb\|AAG44899.1\|AF287966_1 28 kDa major outer membrane protein P28 [_Ehrlichia ewingii_] | 35.4 | 35.4 | 100% | 0.88 |
| AAK98143.1 | major antigenic protein MAP1 [_Ehrlichia ruminantium_] | 32.9 | 32.9 | 90% | 5.1 |
| AAK18727.1 | major antigenic protein MAP1 [_Ehrlichia ruminantium_] | 32.9 | 32.9 | 90% | 5.1 |
| Peptide 2: sfkyennpflgfa (SEQ ID NO: 3) Sequence producing significant alignments: | | | | | |
| ACC85904.1 | p30 [_Ehrlichia canis_] | 46.0 | 46.0 | 100% | 6e-04 |
| ABO36255.1 | Omp-1-15 [_Ehrlichia ewingii_] | 46.0 | 46.0 | 100% | 6e-04 |
| ABX79504.1 | major antigenic protein 1 [_Ehrlichia sp. P-Mtn_] | 46.0 | 46.0 | 100% | 6e-04 |
| ABX79503.1 | major antigenic protein 1 [_Ehrlichia sp. P-Mtn_] | 46.0 | 46.0 | 100% | 6e-04 |
| ABR91963.1 | major antigenic protein 1 [_Ehrlichia ruminantium_] | 46.0 | 46.0 | 100% | 6e-04 |
| ABR91964.1 | major antigenic protein 1 [_Ehrlichia ruminantium_] | 46.0 | 46.0 | 100% | 6e-04 |
| ABR91966.1 | major antigenic protein 1 [_Ehrlichia ruminantium_] | 46.0 | 46.0 | 100% | 6e-04 |
| ABR91965.1 | major antigenic protein 1 [_Ehrlichia ruminantium_] | 46.0 | 46.0 | 100% | 6e-04 |
| ABR91967.1 | major antigenic protein 1 [_Ehrlichia ruminantium_] | 46.0 | 46.0 | 100% | 6e-04 |
| ABD93655.1 | major outer membrane protein P28-15 [_Ehrlichia muris_] | 46.0 | 46.0 | 100% | 6e-04 |
| ABD93658.1 | major outer membrane protein P28-18 [_Ehrlichia muris_] | 46.0 | 46.0 | 100% | 6e-04 |
| ABD93659.1 | major outer membrane protein P28-19 [_Ehrlichia muris_] | 46.0 | 46.0 | 100% | 6e-04 |
| AAD54230.1 | 28 kDa surface antigen protein [_Ehrlichia chaffeensis_] | 46.0 | 46.0 | 100% | 6e-04 |
| AAD54233.1 | 28 kDa surface antigen protein [_Ehrlichia chaffeensis_] | 46.0 | 46.0 | 100% | 6e-04 |
| AAC31546.1 | outer membrane protein P28 precursor [_Ehrlichia chaffeensis_] | 46.0 | 46.0 | 100% | 6e-04 |
| AAK14320.1 | major antigenic protein MAP1 [_Ehrlichia sp. 'South African canine'_] >gb\|AAK98153.1\|AF368013_1 major antigenic protein MAP1 [_Ehrlichia ruminantium_] | 46.0 | 46.0 | 100% | 6e-04 |
| AAK98145.1 | major antigenic protein MAP1 [_Ehrlichia ruminantium_] | 46.0 | 46.0 | 100% | 6e-04 |
| AAK98149.1 | major antigenic protein MAP1 [_Ehrlichia ruminantium_] | 46.0 | 46.0 | 100% | 6e-04 |
| Peptide 3: yetfdvknqgnnykndahryyals (SEQ ID NO: 4) Sequence producing significant alignments: | | | | | |
| ABD93659.1 | major outer membrane protein P28-19 [_Ehrlichia muris_] | 72.7 | 72.7 | 100% | 5e-12 |
| BAD66856.1 | major outer membrane protein P28a [_Ehrlichia muris_] | 72.7 | 72.7 | 100% | 5e-12 |
| AAO12951.1 | 28 kDa outer membrane protein gene 16 [_Ehrlichia chaffeensis_] | 70.2 | 70.2 | 100% | 3e-11 |
| AAO12956.1 | 28 kDa outer membrane protein gene 16 [_Ehrlichia chaffeensis_] | 70.2 | 70.2 | 100% | 3e-11 |
| AAO12941.1 | 28 kDa outer membrane protein gene 16 [_Ehrlichia chaffeensis_] >gb\|AAO12946.1\|AF479836_3 28 kDa outer membrane protein gene 16 [_Ehrlichia chaffeensis_] | 70.2 | 70.2 | 100% | 3e-11 |
| BAD66851.1 | major outer membrane protein P28a-1 [_Ehrlichia sp. HF565_] | 70.2 | 70.2 | 100% | 3e-11 |
| BAD66846.1 | major outer membrane protein P28a [_Ehrlichia sp. Shizuoka-36_] >dbj\|BAD66850.1\|major outer membrane protein P28a [_Ehrlichia sp. Shizuoka-37_] | 70.2 | 70.2 | 100% | 3e-11 |

TABLE 2-continued

Analysis of the peptides showing homology to other Ehrlichia species

| Accession | Description | Max score | Total score | Query coverage | E value |
|---|---|---|---|---|---|
| BAD66853.1 | major outer membrane protein P28a-3 [Ehrlichia sp. HF565] | 70.2 | 70.2 | 100% | 3e-11 |
| BAD66852.1 | major outer membrane protein P28a-2 [Ehrlichia sp. HF565] | 70.2 | 70.2 | 100% | 3e-11 |
| BAD66855.1 | major outer membrane protein P28a-5 [Ehrlichia sp. HF565] | 70.2 | 70.2 | 100% | 3e-11 |
| BAD66854.1 | major outer membrane protein P28a-4 [Ehrlichia sp. HF565] | 70.2 | 70.2 | 100% | 3e-11 |
| AAD54230.1 | 28 kDa surface antigen protein [Ehrlichia chaffeensis] | 64.3 | 64.3 | 100% | 2e-09 |
| AAD54233.1 | 28 kDa surface antigen protein [Ehrlichia chaffeensis] | 64.3 | 64.3 | 100% | 2e-09 |
| AAL12923.1 | outer membrane protein P28 [Ehrlichia chaffeensis] | 64.3 | 64.3 | 100% | 2e-09 |
| AAL12919.1 | outer membrane protein P28 [Ehrlichia chaffeensis] | 64.3 | 64.3 | 100% | 2e-09 |
| AAO12958.1 | 28 kDa outer membrane protein gene 19 [Ehrlichia chaffeensis] | 64.3 | 64.3 | 100% | 2e-09 |
| AAC31548.1 | outer membrane protein P28 precursor [Ehrlichia chaffeensis] | 64.3 | 64.3 | 100% | 2e-09 |
| ABD93655.1 | major outer membrane protein P28-15 [Ehrlichia muris] | 60.9 | 60.9 | 95% | 2e-08 |
| ABD93658.1 | major outer membrane protein P28-18 [Ehrlichia muris] | 60.9 | 60.9 | 95% | 2e-08 |
| ABD93657.1 | major outer membrane protein P28-17 [Ehrlichia muris] | 60.9 | 60.9 | 95% | 2e-08 |
| AAC31546.1 | outer membrane protein P28 precursor [Ehrlichia chaffeensis] | 60.9 | 60.9 | 100% | 2e-08 |
| AAD54231.1 | 28 kDa surface antigen protein [Ehrlichia chaffeensis] | 60.9 | 60.9 | 100% | 2e-08 |
| AAL12922.1 | outer membrane protein P28 [Ehrlichia chaffeensis] | 60.9 | 60.9 | 100% | 2e-08 |

P28 Peptides were Recognized by Anti-*Ehrlichia* Antibody in Mice Infected with *Ehrlichia muris*.

Figure 2:
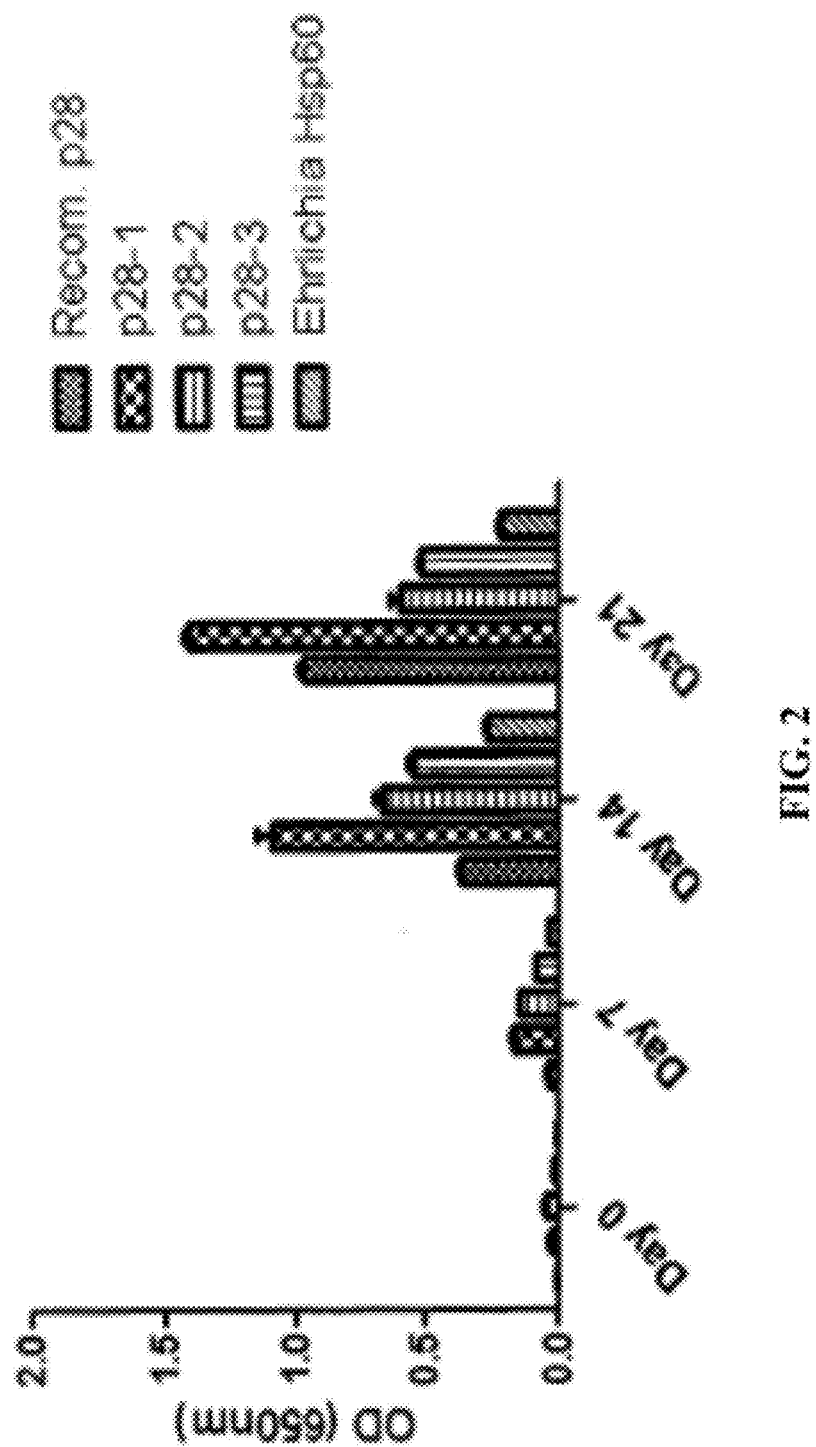
FIG. 2 shows the detection of $Ehrlichia$ antibody in sera of mice infected with $E.$ $muris$ using different P28 peptides.
Figure 3:
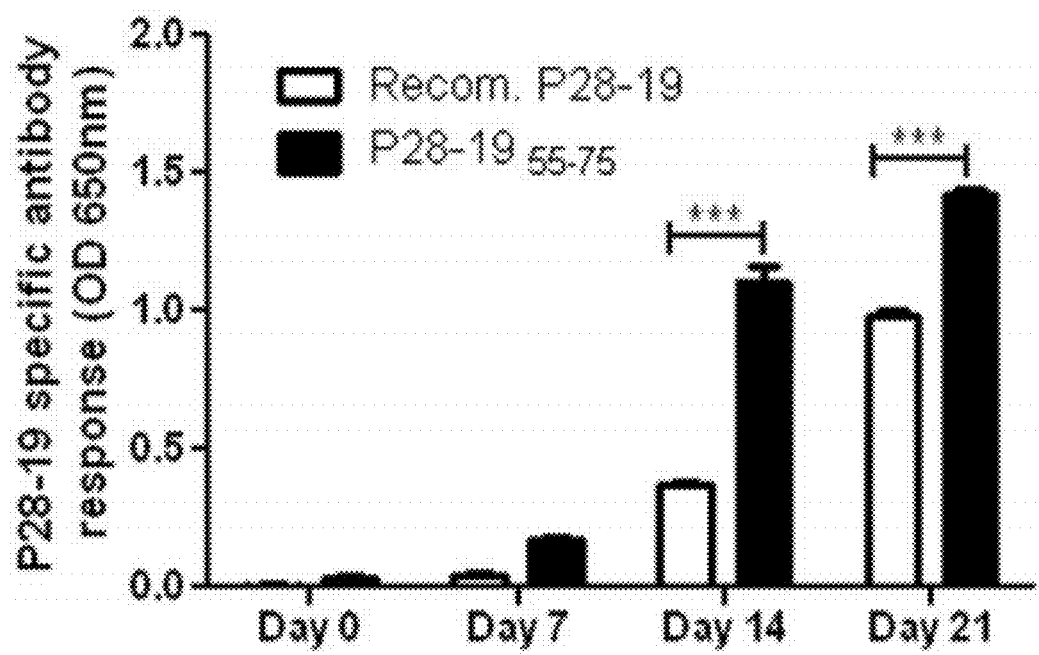
FIG. 3 shows P28-19$_{55-75}$ peptide reacted with $E.$ $muris$ antibody. The peptide corresponding to the predicted hydrophilic sequence of amino acids 55-75 of P28-19 reacted with $Ehrlichia$ antibody. The peptide was found to be more sensitive in reacting with the $Ehrlichia$ antibody than the recombinant P28-19 protein (***$p<0.001$ as determined by Student t test).

All the three peptides reacted with *Ehrlichia muris* antibodies in the sera of infected mice. However, peptide 1 was found to be more sensitive in detecting the *Ehrlichia*-specific antibody (FIG. 2). The peptide could detect *Ehrlichia* antibody even on day 7. Hence peptide 1 was further used for detection of the *Ehrlichia* antibodies in other infected animals. The P28 peptide was also found to be more sensitive for the detection of *Ehrlichia* antibodies than the recombinant P28 protein (FIG. 3).

P28 Reacted with *Ehrlichia* Antibody from Infected Dogs and Humans.

As the peptide 1 of P28-19 was more sensitive than the other peptides, this peptide was used to detect *Ehrlichia* antibody from dogs infected with *E. canis, E. chaffeensis* and *E. ewingii* (FIG. 4). The P28 peptide was very sensitive in detecting *Ehrlichia* antibodies of dogs infected with each of the three species of *Ehrlichia*. The P28 was also sensitive for detection of *Ehrlichia* antibody in human serum.

These P28-19 peptides were also used to determine antibody production when mice were vaccinated with *Ehrlichia* Hsp60 peptides followed by challenge with *E. muris*. Vaccinated mice produced large amount of antibodies compared to unvaccinated mice.

P28 Peptides do not Cross-React with Antibodies of *Rickettsia* Species or *Orientia*.

Figures 4A, 4B, 4C, 4D:
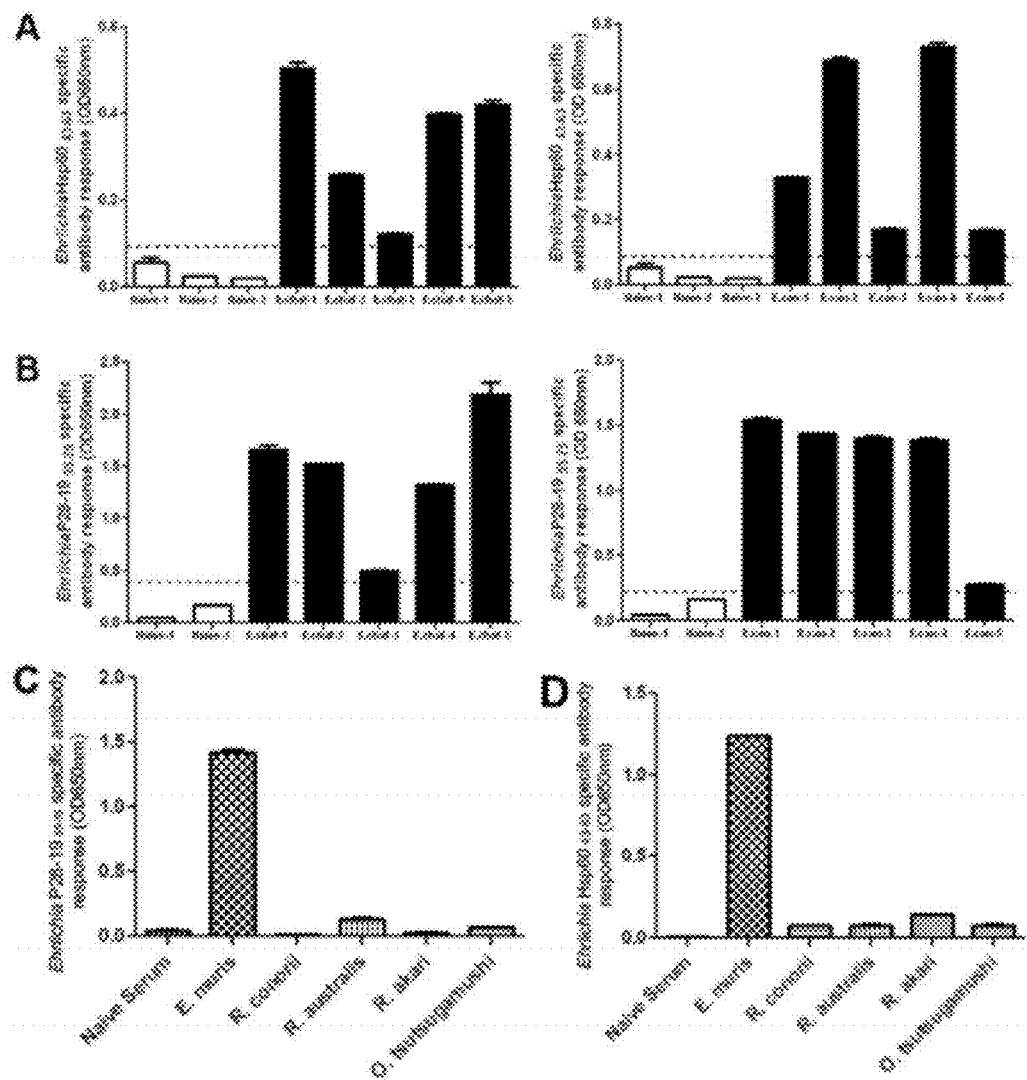
FIGS. 4A-4D shows $Ehrlichia$ Hsp60$_{43-63}$ and P28-19$_{55-75}$ peptides reacted with $Ehrlichia$-specific antibody from dogs infected with $E.$ $canis$ and $E.$ $chaffeensis$. (A) $Ehrlichia$ Hsp60$_{43-63}$ peptide reacted with antibodies from five dogs infected with $E.$ $chaffeensis$ and five dogs infected with $E.$ $canis$. (B) P28-19$_{55-75}$ peptide reacted with antibodies from five dogs infected with $E.$ $chaffeensis$ and five dogs infected with $E.$ $canis$. Each bar represents the mean of three replicates. The horizontal line in the graphs represents Mean±3 SD of negative samples. The positive samples are significantly different from negative samples. (C) P28-19$_{55-75}$ peptide did not react with antibodies from mice infected with $Rickettsia$ or $Orientia$. (D) $Ehrlichia$ Hsp60$_{43-63}$ peptide did not react with antibodies from mice infected with $Rickettsia$ or $Orientia$.

The P28 peptides did not cross-react with other species of the family Rickettsiaceae (*R. conorii, R. australis, R. akari* and *O. tsutsugamushi* demonstrating that the P28 peptides only react with *ehrlichia* antibodies (FIGS. 4C-4D).

Immunofluorescence Microscopic Detection of *E. muris* with Antibodies Produced Against the Peptide P28-19-1.

As the peptide P28-19-1 was found to be very sensitive in detection by ELISA and produced highly sensitive antibodies than other peptides, they were used to detect *E. muris* by immunofluorescence microscopy. The antibody produced against P28-19-1 could detect *E. muris* in infected DH82 cells, whereas the naïve antibody could not detect any pathogen.

The Peptides of P28-19 55-75 and *Ehrlichia* Hsp60 43-63 Functioned as Vaccines to Protect Against the Pathogen.

Figures 5A, 5B:
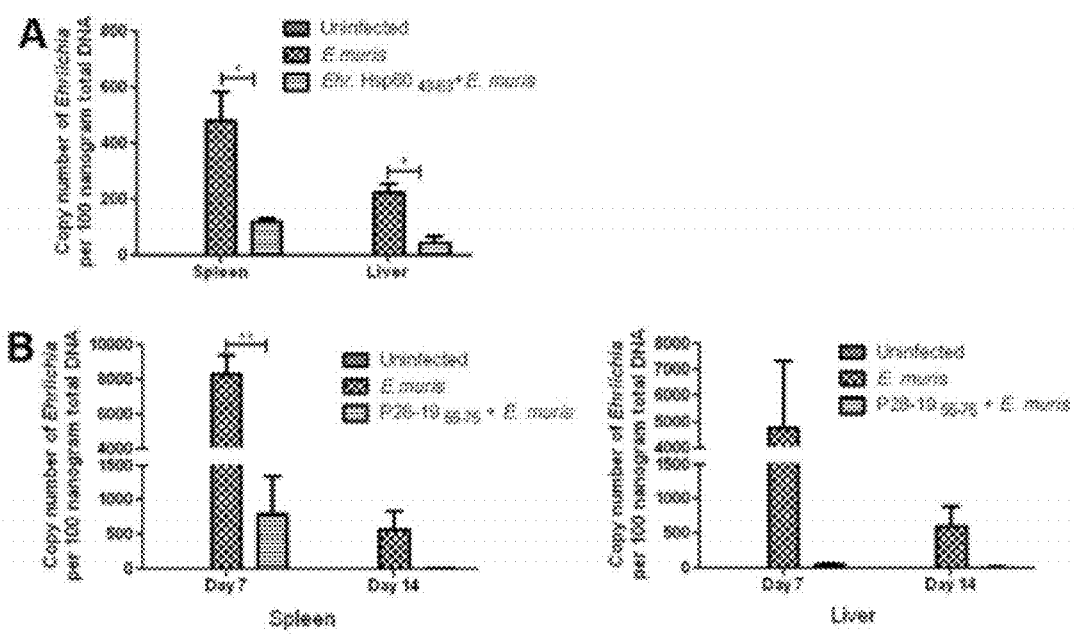
FIGS. 5A-5B shows immunization with $Ehrlichia$ Hsp60$_{43-63}$ and P28-19$_{55-75}$ peptides protected mice from $Ehrlichia$ infection. (A) Mice immunized with $Ehrlichia$ Hsp60$_{43-63}$ were protected against $E.$ $muris$ challenge as determined by the bacterial load measured by quantitative real time-PCR on day 14 after $E.$ $muris$ challenge (*$p<0.05$ as determined by t test). (B) Mice immunized with P28-19$_{55-75}$ peptide was protected against $E.$ $muris$ challenge as determined by the bacterial load measured by quantitative real time-PCR on days 7 and 14 after $E.$ $muris$ challenge (**$p<0.01$ as determined by t test).

Since the P28-19$_{55-75}$ and *Ehrlichia* Hsp60$_{43-63}$ epitope peptides induced antibodies, the inventors reasoned that they also could provide protection against Ehrlichia thereby functioning as potential vaccine candidates. To prove our hypothesis mice were injected with P28-19$_{55-75}$ or *Ehrlichia* Hsp60$_{43-63}$ epitope peptides and challenged 30 days later with *E. muris*. The spleen and liver were collected at different days after bacterial challenge and the bacterial copy number determined by quantitative real time PCR. A lower bacterial load was observed in both spleen and liver on days 7 and 14 after bacterial infection in the vaccinated mice compared to unvaccinated controls (FIG. 5). The results demonstrated that P28-19$_{55-75}$ and *Ehrlichia* Hsp60$_{43-63}$ peptides functioned as vaccine candidates and provided protection against Ehrlichia infection.

Figure 6A:
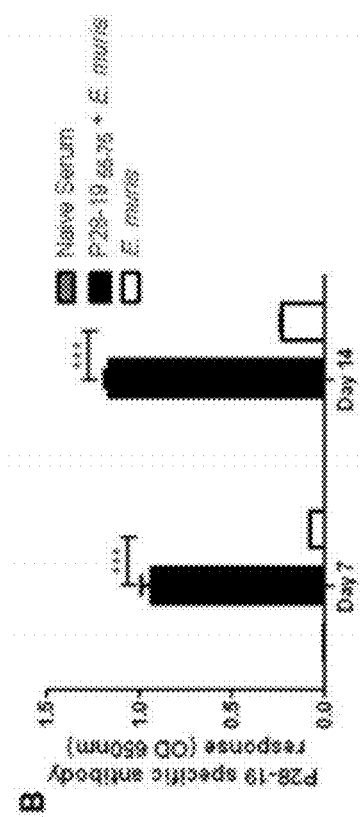
FIGS. 6A-6B shows protection induced by $Ehrlichia$ Hsp60$_{43-63}$ and P28-19$_{55-75}$ peptides was associated with induction of $Ehrlichia$-specific IgG antibody. (A) $Ehrlichia$ Hsp60$_{43-63}$ vaccinated mice induced higher IgG antibody levels after challenge with $E.$ $muris$ compared to unvaccinated $E.$ $muris$-infected mice (*$p<0.001$ as determined by t test). (B) P28-19$_{55-75}$ peptide vaccinated mice induced higher IgG antibody levels after $E.$ $muris$ challenge compared to unvaccinated $E.$ $muris$-infected mice (*$p<0.001$ as determined by Student t test).
Figure 6B:
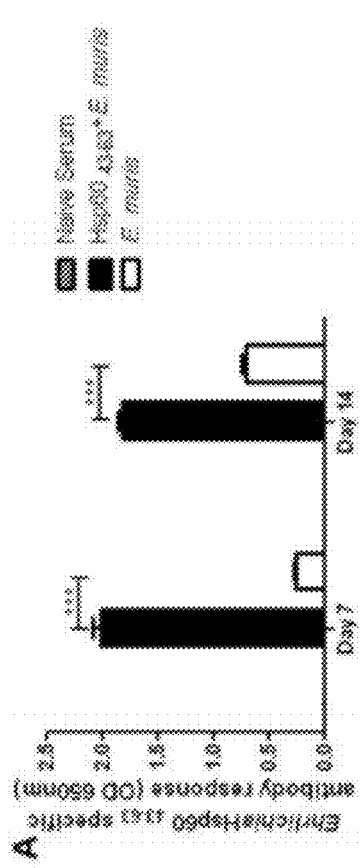

Immunization with vaccines stimulates the immune system to produce a robust antibody response that can provide protection against pathogens. To determine the antibody responses against the *Ehrlichia* Hsp60$_{43-63}$ peptide vaccine, blood was collected from vaccinated mice on days 7 and 14 and performed ELISA. There was a significant difference in the antibody response between unvaccinated and *Ehrlichia* Hsp60$_{43-63}$ vaccinated mice after challenge with *E. muris*. However, there was no difference between the antibody levels in vaccinated mice between days 7 and 14. The *Ehrlichia* Hsp60$_{43-63}$-specific antibody levels in infected unvaccinated mice were highest on day 14 compared to day 7 (FIG. 6A). To determine the antibody responses against the P28-19$_{55-75}$ peptide vaccine, we collected blood from immunized mice on days 7 and 14 and subjected the samples to ELISA. There was a significant difference in the antibody response between unvaccinated and P28-19$_{55-75}$ vaccinated mice after challenge with *E. muris*. Antibody levels were higher on day 14 compared to day 7 (FIG. 6B).

Figure 7A:
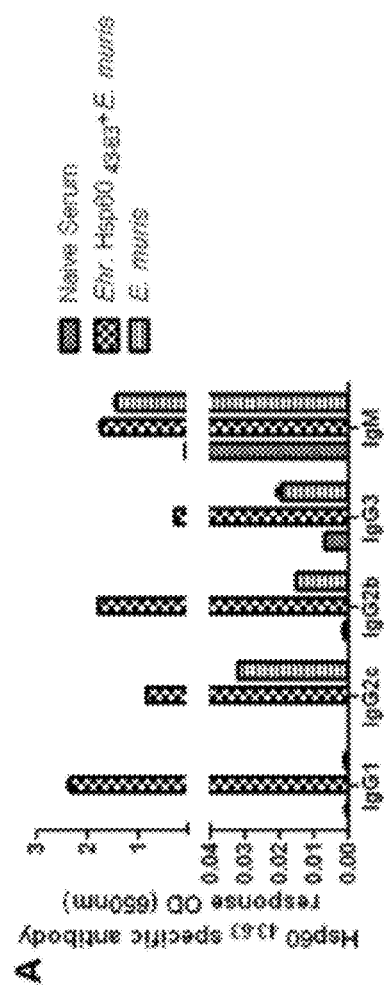
FIGS. 7A-7B shows antibody isotypes in mice immunized with $Ehrlichia$ Hsp60$_{43-63}$ and P28-19$_{55-75}$ peptides. (A) Mice vaccinated with $Ehrlichia$ Hsp60$_{43-63}$ peptide had higher levels of IgG1, IgG2c, IgG2b, and IgG3 compared to unvaccinated mice after bacterial challenge. (B) Mice vaccinated with P28-19$_{55-75}$ peptide had higher levels of IgG1, IgG2b, IgG2c, and IgG3 compared to unvaccinated mice after bacterial challenge. The data were expressed as mean plus standard deviation and three mice per group were included for analysis.
Figure 7B:
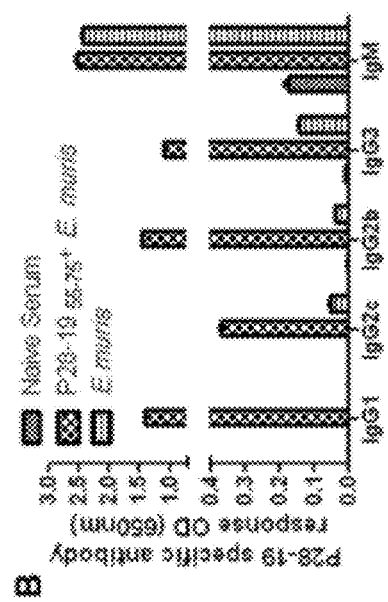

As antibody isotype responses can be useful indicators of immune bias during infection (Fairlie-Clarke et al. (2010) BMC Immunol 11:6), antibody isotypes were determined after vaccination with the peptide epitopes. The level of antibody isotypes increased by day 14 compared to day 7 after bacterial challenge (data not shown). The *Ehrlichia* Hsp60$_{43-63}$-vaccinated mice had higher levels of IgG1, IgG2c, IgG2b, IgG3 and IgM after bacterial challenge compared to unvaccinated mice on day 14 (FIG. 7A). The isotypes of the antibodies of P28-19 peptide in vaccinated and unvaccinated mice after challenge with *E. muris* (day 14 post challenge) were analyzed by ELISA. The P28-19$_{55-75}$ vaccinated mice challenged with *E. muris* had higher levels of IgG1, IgG2b, IgG3 and IgM compared to unvaccinated mice infected with the pathogen (FIG. 7B).

*Ehrlichia* Hsp60 and P28-19 Specific Memory CD4+ Th1 Responses are Induced During *E. muris* Infection.

Figures 8A, 8B:
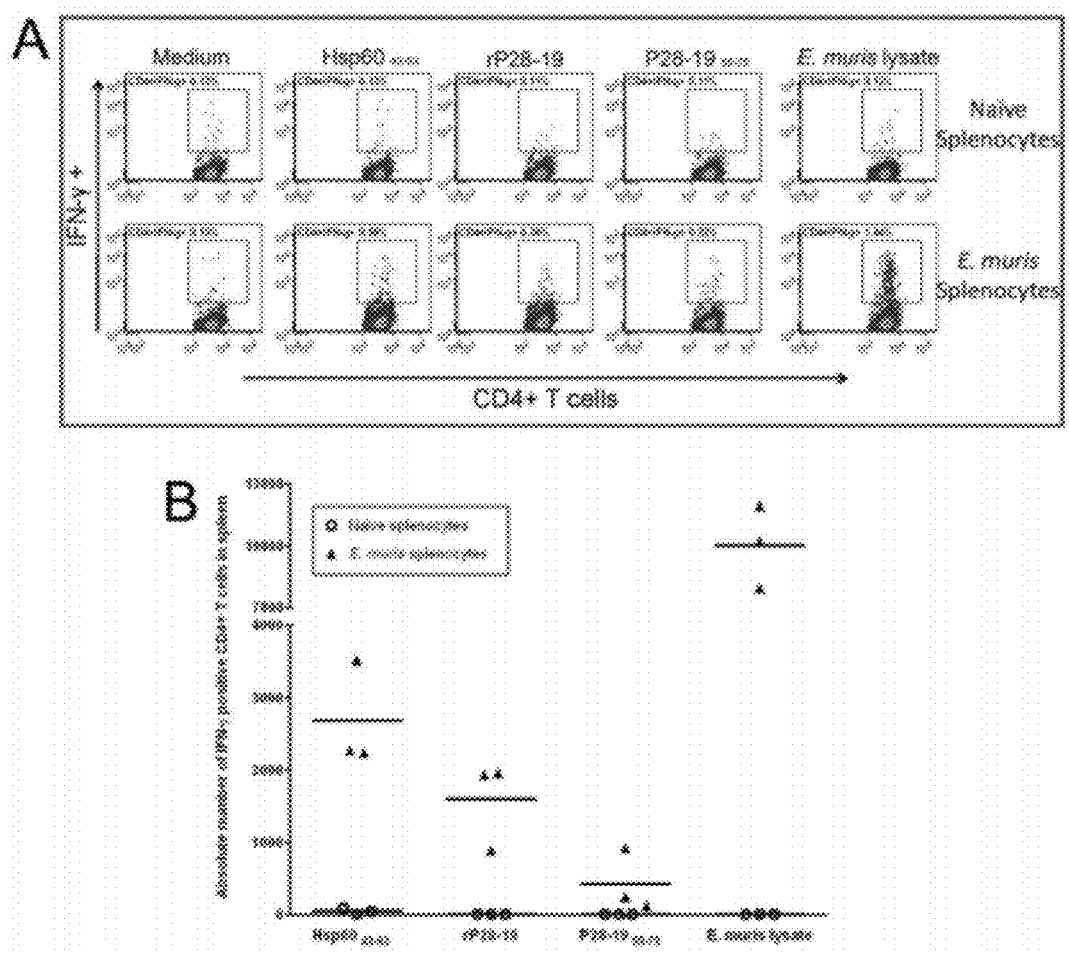
FIGS. 8A-8B shows *Ehrlichia* Hsp60$_{43-63}$ and P28-19$_{55-75}$-specific memory CD4+ T cells develop during *E. muris* infection. The inventors determined by flow cytometry the frequencies and absolute numbers of *Ehrlichia* Hsp60$_{43-63}$- and P28-19-specific IFN-γ-producing CD4+ T cells in the spleen of mice infected with *E. muris*. (A) Mice infected with *E. muris* had higher frequency of *Ehrlichia* Hsp60$_{43-63}$- and P28-19$_{55-75}$-specific IFN-γ-producing CD4+ T cells in the spleen on day 45 after infection compared to naive uninfected mice. Representative dot plots were gated on live cells followed by CD3+ T cells. (B) Absolute numbers of *E. muris*-specific IFN-γ-producing CD4+ T cells in the spleen of the same mice detected following in vitro stimulation with the *Ehrlichia* Hsp60$_{43-63}$, P28-19$_{55-75}$ peptides; rP28-19 and *E. muris* whole cell lysate are shown for comparison. Horizontal bars represent the mean; data are representative of two independent experiments (n=3 animals per group).

Flow cytometry was used to determine if *Ehrlichia* Hsp60$_{43-63}$ and P28-19 specific memory T cells are induced during *E. muris* infection. Splenocytes from *E. muris*-infected mice were harvested on day 45 post-infection and stimulated in vitro with the *Ehrlichia* Hsp60$_{43-63}$ and P28-19$_{55-75}$ for 18 h. Compared to uninfected naive mice, *E. muris*-infected mice had significantly higher frequencies and absolute numbers of *Ehrlichia* Hsp60$_{43-63}$ and P28-19$_{55-75}$ specific IFN-$\gamma$-producing CD4+ Th1 cells in their spleen (FIG. 8).

B. Materials and Methods

Design of P28-19 and *Ehrlichia* Hsp60 Peptides.

To determine a protein sequence for potential antigenic epitopes, sequences that are hydrophilic, surface-oriented, and flexible are selected. Most naturally occurring proteins in aqueous solutions have their hydrophilic residues on the protein surface and hydrophobic residues buried in the interior. Three regions of the *E. muris* P28-19 and Hsp60 protein sequence had good hydrophilicity predicted by the Lasergene software (DNAStar, WI, USA). Hydrophilic sequences of both the *Ehrlichia* P28-19 and Hsp60 proteins were selected with no hydrophobic residues. The hydrophilic regions of P28-19 correspond to amino acids 55-75, 91-103, and 124-145 of SEQ ID NO:1. The hydrophilic regions of *Ehrlichia* Hsp60 correspond to amino acids 43-63, 179-199, and 387-406 of SEQ ID NO:5. The sequences showed homology to other *Ehrlichia* species. The peptides were synthesized and conjugated to KLH (Biosynthesis, Lewisville, Tex.) and used as probes to detect antibodies to *E. canis* and *E. chaffeensis* or to raise antibodies.

3D Structure Prediction.

The 3D structure of P28-19 was modeled using the online I-TASSER (iterative threading assembly refinement) server. I-TASSER builds 3D models from an amino acid sequence using fold recognition and multiple-threading alignments by LOMETS, a meta-threading server at the Univ. of Michigan which combines seven state-of-the art threading programs (FUGUE, HHsearch, MUSTER, PROSPECT, PPA, SP3 and SPARK) then performs iterative structural assembly simulations. The function of the predicted models is then inferred by structurally matching the 3D models with known proteins using protein function databases. The best predicted model from I-TASSER gave a C-score of $-3.338$, a TM-score of $0.34\pm0.12$, and an Exp. RMSD of $14.1\pm3.8$. The C-score is a confidence value for estimating the quality of the model and generally ranges from $[-5, 2]$ with a higher score being better; TM-scores measure structural similarity and are used to measure the accuracy of structural modeling with a TM-score $>0.5$ indicating a model having the correct topology and a TM-score $<0.17$ showing random similarity. RMSD is simply the average distance of all amino acid pairs between two structures. Protein segments that are relatively unstructured such a loops and coils can result in high RMSD scores. Based on these results a beta-barrel portion of the model is likely to be a reasonable representation of the 3D structure of body of the protein. The coils however, which were modeled ab initio, are likely idiosyncratic and there is no way to verify their structure without doing x-ray crystallography or NMR. The inventors double-checked this model against the best model produced by Phyre2 with similar results. Thus, this model should be approached with caution and care taken not to over-interpret the structure of the loops and coils.

The 3D structure of *Ehrlichia* Hsp60 was modeled using the online Phyre2 server (Kelley and Sternberg (2009) Nature Protocols 4:363-371). Phyre2 aligns hidden Markov models via HHsearch to improve alignment accuracy and detection rate. In "intensive" mode, which was used here, Phyre2 also incorporates Poing (Jefferys et al. (2010) J Mol Biol 397: 1329-1338), a new ab initio folding simulation based on Langevin dynamics, to model regions of the protein that have no detectable homology with known structures. For our Hsp60 sequence, 100% of the residues were modeled at >90% confidence level. The top three PDB models, all GroEL chaperone proteins, had 100% confidence levels and sequence identities of 51-56%. While the model presented is likely to be a reasonable estimate of the true 3D structure of this protein, there is no way to validate this so caution should be used in its interpretation.

Detection of anti-Ehrlichia antibodies using the *Ehrlichia* Hsp60$_{43-63}$ and P28-19$_{55-75}$ peptides. The inventors used ELISA to detect *Ehrlichia* antibodies in the sera of infected mice and dogs. Two hundred fifty nanograms of the peptides were coated on an ELISA plate (MaxiSorp, Nunc, Denmark) for 1 hour at room temperature. After washing, the plates were blocked with 5% FCS (in PBS-Tween) for 1 hour. The plates were further incubated with sera of infected mice or dogs for 1 hour at room temperature. Washing was followed by incubation with secondary antibody conjugated to alkaline phosphatase (AP) (Kirkegaard and Perry Laboratories, Gaithersburg, Md.) for 1 hour. After the addition of substrates (Blue Phos™ phosphatase substrate, Kirkegaard and Perry Laboratories, Gaithersburg, Md.), optical densities were measured using an ELISA plate reader (Molecular Devices, Sunnyvale, Calif.) at 650 nm after 30 min. incubation at room temperature. All assays were performed in triplicate wells, and the average values were calculated.

Mice.

Six to eight-week old female C57BL/6 mice were used in all experiments. Mice were purchased from the Jackson Laboratory (Bar Harbor, Me.) and housed and cared for in the animal research center in accordance with the Institutional Animal Care and Use Committee guidelines under whose review and approval the experiments were conducted (Protocol No. 95-09-066).

Immunizations and *Ehrlichia muris* Challenge.

Mice were immunized i.p., with two doses of 50 micrograms (0.02 μM) of each P28-19$_{55-75}$ peptide or *Ehrlichia* Hsp60$_{43-63}$ peptides conjugated to KLH 15 days apart (the first immunization with complete Freund's adjuvant and the second immunization with incomplete Freund's adjuvant) (3 mice per group). Thirty days after the first immunization mice were challenged intraperitoneally (i.p.) with a high dose of *E. muris* (~1×10$^4$ bacterial genomes) and observed daily. Controls included unchallenged naive mice as well as unvaccinated mice injected with *E. muris* alone. Mice were sacrificed on days 7, 14 and 21 after *Ehrlichia* challenge, and spleen and liver were harvested and sera collected. The ehrlichial load in spleen and liver was determined by quantitative RT-PCR. Sera were assayed for determination of antibody titers.

Measurement of Antibody Subclasses.

ELISA was performed to measure the concentration of *E. muris* specific IgG subclass antibodies as described previously [Ismail et al. (2004) J Immunol 172:1786-1800; McBride et al. (2003) Infect Immun 71: 2516-2524). Briefly, the ELISA plates were coated with 50 μl of peptide (Ehrlichia Hsp60$_{43-63}$) or recombinant P28-19 protein at a concentration of 4 μg/ml in PBS. Serum samples were diluted 1:100, and 100 μl of each sample was added to peptide-coated wells and incubated at 25° C. for 1 h. Alkaline phosphatase conjugated goat anti-mouse IgG1, IgG2c, IgG2b, IgG3, or IgM antibodies (SouthernBiotech, Birmingham, Ala.) were added at a dilution of 1:300, and color was developed using Blue Phos™ phosphatase substrate (Kirkegaard and Perry Laboratories, Gaithersburg, Md.). Optical densities were measured using an ELISA plate reader (Molecular Devices, Sunnyvale, Calif.) at 650 nm after 30 min. incubation at room temperature. All assays were performed in triplicate wells, and the average values were calculated. When peptides conjugated to KLH were used as a probe in ELISA, KLH was used as control and the results subtracted from positive values.

Fluorescence Microscopy.

P28-19$_{55-75}$ peptides were injected (i.p.—two times, 15 days apart) into C57BL/6 mice. Antibody was obtained 40 days after the first injection. *E. muris* infected DH82 cells were fixed in 50% methanol-acetone for 5 minutes and later incubated with the anti-Ehrlichia P28-19$_{55-75}$ antibody (or naive antibody as control) (1:125) (45 min). After three washes in PBS they were reacted with anti-mouse immunoglobulin G conjugated to Alexa 488. Finally they were mounted in mounting medium containing DAPI (Vectashield, Vector Labs, Burlingame, Calif.). Experiments were repeated three times. The cells were viewed by epifluorescence microscopy (Olympus BX51, Japan).

Assessment of Ehrlichial Load in Organs by Quantitative Real-Time PCR.

The bacterial burdens in the organs were determined by quantitative real-time PCR. The *Ehrlichia*-specific dsb gene, which encodes a disulfide bond-forming protein (GenBank accession #AY236484 and AY236485), was selected as the target gene for amplification of *E. muris*. The sequences of the primers and probes and thermal cycle conditions were described previously (Stevenson et al. (2006) Infect Immun 74:4856-4864). PCR analyses were considered negative for ehrlichial DNA if the critical threshold values (Ct) exceeded 40 cycles. Expression of the ehrlichial load was normalized relative to the total DNA. Each sample was run in duplicate.

Assessment of Hsp60- and P28-19-Specific Memory CD4+ T Cell Responses in *E. muris*-Infected Mice.

The frequencies of antigen specific IFN-γ-producing T cells in the spleens were determined by flow cytometric analysis. Splenocytes of individual mice were cultured in vitro in a 12-well plate at a concentration of 5×10$^6$ cells per well in complete medium (RPMI 1640 medium containing 10% heat-inactivated fetal bovine serum, 10 mM HEPES buffer, 50 μM 2-mercaptoethanol, and antibiotics [penicillin 100 units/ml and streptomycin 100 μg/ml]) in the presence of Hsp60$_{43-63}$ peptide, P28-19$_{55-75}$ peptide, recombinant P28-19 or *E. muris* whole cell lysate antigen (5 μg/ml). Positive and negative control wells contained concanavalin A at a concentration of 5 μg/ml or medium, respectively. The cells were harvested after 18 hours of in vitro antigen stimulation (100 microgram per well) followed by 4 hour incubation with Brefeldin A (BD GolgiPlug, BD Biosciences, San Diego, Calif.) and stained with specific antibodies as described below.

After blocking Fc receptors with anti-Fc receptor mAbs (BD PharMingen, San Diego, Calif.) in FACS buffer (Dulbecco's PBS without Mg$^{2+}$ or Ca$^{2+}$ containing 1% fetal calf serum and 0.09% sodium azide) at 4° C. for 15 minutes, cells were labeled with fluorochrome-conjugated mAbs (BD Biosciences Pharmingen, San Diego, Calif.) specific for mouse CD3 (APC; clone 17A2), and CD4 (FITC; clone RM4-5), and CD8 (PerCP-Cy 5.5; clone 53-6.7). Later, the cells were fixed, permeabilized and stained for intracellular IFN-γ (PE; clone XMG1.2) using BD Cytofix/Cytoperm Fixation/Permeabilization kit following the manufacturer's instructions. Flow cytometric data were collected using FACSCanto (BD Immunocytometry Systems, San Jose, Calif.). Live cells were gated based on a vital dye (Near-IR Live/dead fixable dead cell stain; Invitrogen, Carlsbad, Calif.), and a total of 200,000 events were collected. Data were analyzed using FCS Express software (De Novo Software, Los Angeles, Calif.). Dot plots were gated on CD3+ T cells and the frequencies and absolute numbers of antigen-specific IFN-γ-producing CD4+ T cells in the spleens were determined after subtracting the background staining of unstimulated cells in wells containing medium only.

Statistical Analysis.

When indicated, unpaired two-tailed t test was used for comparison of two groups using GraphPad Prism (GraphPad Software Inc., La Jolla, Calif.). Statistical significance was determined at 95% (p<0.05).

The invention claimed is:

1. An isolated *Ehrlichia* peptide having a sequence at least 80% identical to the amino acid sequence of SEQ ID NOS: 2, 3, or 4, and wherein the isolated peptide is 16 to 25 amino acids in length.

2. The peptide of claim 1, wherein said peptide is at least 90% identical to the amino acid sequence of SEQ ID NOS: 2, 3, or 4.

3. The peptide of claim 1, wherein said peptide is at least 95% identical to the amino acid sequence of SEQ ID NOS: 2, 3, or 4.

4. The peptide of claim 1, wherein said peptide is coupled to a label.

5. The peptide of claim 4, wherein said peptide is conjugated to a carrier.

6. The peptide of claim 5, wherein said peptide and carrier are conjugated by glutaraldehyde, m-maleimidobenzoyl-N-hydroxy- succinimide ester, carbo-diimide or bis-biazotized benzidine.

7. The peptide of claim 5, wherein said carrier is keyhole limpet hemocyanin, human serum albumin, a lymphokine, or an adjuvant.

8. The peptide of claim 7, wherein the adjuvant is IL2, IL4, IL8, BCG, Detox, RIBI, ISCOMS, or aluminum hydroxide.

9. A method of detecting *Ehrlichia,* comprising the steps of:
contacting a sample with a peptide of claim 1; and
detecting an antibody/peptide complex, wherein detection of a complex indicates the presence of *Ehrlichia*.

10. The method of claim 9, wherein the sample is from a canine.

11. The method of claim 9, wherein said sample is serum.

12. A diagnostic kit for detecting *Ehrlichia*, said kit comprising: an isolated peptide of claim 1 and a detection reagent.

13. The kit of claim 12, wherein the peptide is coupled to a label.

14. The kit of claim 13, wherein the label is selected from the group consisting of luciferase, horseradish peroxidase, P galactosidase galactosidase, and fluorescent labels.

15. The peptide of claim 1, wherein said peptide has the amino acid sequence of SEQ ID NOS: 2, 3, or 4, and wherein the isolated peptide is 16 to 25 amino acids in length.

\* \* \* \* \*

SEQUENCE LISTING

<160> NUMBER OF SEQ ID NOS: 8

<210> SEQ ID NO 1
<211> LENGTH: 275
<212> TYPE: PRT
<213> ORGANISM: Ehrlichia muris

<400> SEQUENCE: 1

```
Met Asn Cys Lys Arg Ile Phe Ile Lys Ser Ala Leu Ile Ser Leu Ile
1               5                   10                  15

Ser Phe Leu Pro Gly Ile Ser Phe Ser Asp Pro Ile Gln Asp Ser Asn
                20                  25                  30

Val Ser Gly Asn Phe Tyr Ile Ser Gly Lys Tyr Met Pro Ser Ala Ser
            35                  40                  45

His Phe Gly Val Phe Ser Ala Lys Glu Glu Lys Asn Ala Thr Ala Lys
        50                  55                  60

Thr Phe Gly Leu Lys Gln Asp Trp Asp Gly Ala Ala Ile Ser Asn Thr
65                  70                  75                  80

Ser Thr Asp Val Phe Thr Ile Ser Asn Tyr Ser Phe Lys Tyr Glu Asn
                85                  90                  95

Asn Pro Phe Leu Gly Phe Ala Gly Ala Ile Gly Tyr Ser Met Gly Gly
                100                 105                 110

Pro Arg Ile Glu Phe Glu Val Ser Tyr Glu Thr Phe Asp Val Lys Asn
                115                 120                 125

Gln Gly Asn Asn Tyr Lys Asn Asp Ala His Arg Tyr Tyr Ala Leu Ser
            130                 135                 140

Gln Asp Thr Thr Ile Ala Gln Asn Lys Phe Val Val Leu Lys Asn Glu
145                 150                 155                 160

Gly Leu Ala Asp Ile Ser Phe Met Leu Asn Ala Cys Tyr Asp Val Thr
                165                 170                 175

Thr Glu Gly Ile Pro Phe Ser Pro Tyr Ile Cys Ala Gly Ile Gly Thr
                180                 185                 190

Asp Leu Val Ser Met Phe Glu Ala Thr Ser Pro Lys Ile Ser Tyr Gln
                195                 200                 205

Gly Lys Leu Gly Leu Ser Tyr Ser Ile Ser Pro Glu Thr Ser Val Phe
210                 215                 220

Val Gly Gly His Phe His Lys Val Val Gly Asn Glu Phe Lys Asp Val
225                 230                 235                 240

Pro Ala Ile Val Pro Ser Gly Ser Thr Leu Ala Gly Asn His Phe Ala
                245                 250                 255

Ile Val Thr Leu Asn Val Cys His Phe Gly Ile Glu Leu Gly Gly Arg
                260                 265                 270

Phe Ala Phe
        275

<210> SEQ ID NO 2
<211> LENGTH: 16
<212> TYPE: PRT
<213> ORGANISM: Ehrlichia muris

<400> SEQUENCE: 2

Ala Lys Glu Glu Lys Asn Ala Thr Ala Lys Thr Phe Gly Leu Lys Gln
1               5                   10                  15

<210> SEQ ID NO 3
<211> LENGTH: 20
<212> TYPE: PRT
<213> ORGANISM: Ehrlichia muris

<400> SEQUENCE: 3

Ser Phe Lys Tyr Glu Asn Asn Pro Phe Leu Gly Phe Ala Gly Ala Ile
1               5                   10                  15

Gly Tyr Ser Met
            20
```

```
<210> SEQ ID NO 4
<211> LENGTH: 24
<212> TYPE: PRT
<213> ORGANISM: Ehrlichia muris

<400> SEQUENCE: 4

Tyr Glu Thr Phe Asp Val Lys Asn Gln Gly Asn Asn Tyr Lys Asn Asp
1               5                   10                  15

Ala His Arg Tyr Tyr Ala Leu Ser
            20

<210> SEQ ID NO 5
<211> LENGTH: 406
<212> TYPE: PRT
<213> ORGANISM: Ehrlichia muris

<400> SEQUENCE: 5

Met Ala Asn Val Val Thr Gly Glu Gln Leu Asp Lys Ser Ile Arg
1               5                   10                  15

Glu Val Val Arg Ile Leu Glu Asp Ala Val Gly Cys Thr Ala Gly Pro
                20                  25                  30

Lys Gly Leu Thr Val Ala Ile Ser Lys Ser Tyr Gly Ala Pro Glu Ile
            35                  40                  45

Thr Lys Asp Gly Tyr Lys Val Ile Lys Ser Ile Lys Pro Glu Asp Pro
50                  55                  60

Leu Ala Leu Ala Ile Ala Asn Ile Ile Thr Gln Ser Ala Ser Gln Cys
65                  70                  75                  80

Asn Asp Lys Val Gly Asp Gly Thr Thr Thr Cys Ser Ile Leu Thr Ala
                85                  90                  95

Lys Val Ile Glu Glu Val Ser Lys Ala Lys Ala Gly Ala Asp Ile
            100                 105                 110

Val Cys Ile Lys Glu Gly Val Leu Lys Ala Lys Glu Ala Val Leu Glu
        115                 120                 125

Ala Leu Met Ser Met Lys Arg Glu Val Leu Ser Glu Glu Ile Ala
    130                 135                 140

Gln Val Ala Thr Ile Ser Ala Asn Gly Asp Lys Asn Ile Gly Ser Lys
145                 150                 155                 160

Ile Ala Gln Cys Val Gln Glu Val Gly Lys Asp Gly Val Ile Thr Val
                165                 170                 175

Glu Glu Ser Lys Gly Phe Lys Glu Leu Asp Val Glu Lys Thr Asp Gly
            180                 185                 190

Met Gln Phe Asp Arg Gly Tyr Leu Ser Pro Tyr Phe Val Thr Asn Ser
        195                 200                 205

Glu Lys Met Leu Val Glu Phe Glu Asn Pro Tyr Ile Leu Leu Thr Glu
    210                 215                 220

Lys Lys Leu Asn Ile Ile Gln Pro Ile Leu Pro Ile Leu Glu Asn Val
225                 230                 235                 240

Ala Arg Ser Gly Arg Pro Leu Leu Ile Ile Ala Glu Asp Val Glu Gly
                245                 250                 255

Glu Ala Leu Ser Thr Leu Val Leu Asn Lys Leu Arg Gly Gly Leu His
            260                 265                 270

Val Ala Ala Val Lys Ala Pro Gly Phe Gly Asp Arg Arg Lys Asp Met
        275                 280                 285

Leu Gly Asp Ile Ala Ile Leu Thr Gly Ala Lys His Val Ile Ser Asp
    290                 295                 300

Asp Leu Ala Ile Lys Met Glu Asp Leu Thr Leu Ala Glu Leu Gly Thr
305                 310                 315                 320
```

```
Ala Lys Asn Ile Arg Ile Thr Lys Asp Thr Thr Thr Ile Ile Gly Ser
                325                 330                 335

Val Asp Asn Ser Ser Thr Asn Val Gln Ser Arg Ile Asn Gln Ile Lys
            340                 345                 350

Met Gln Ile Glu Ala Ser Thr Ser Asp Tyr Asp Lys Glu Lys Leu Arg
            355                 360                 365

Glu Arg Leu Ala Lys Leu Ser Gly Gly Val Ala Val Leu Lys Val Gly
        370                 375                 380

Gly Ser Ser Glu Val Glu Val Lys Glu Arg Lys Asp Arg Val Glu Asp
385                 390                 395                 400

Ala Leu His Ala Thr Arg
                405

<210> SEQ ID NO 6
<211> LENGTH: 21
<212> TYPE: PRT
<213> ORGANISM: Ehrlichia muris

<400> SEQUENCE: 6

Tyr Gly Ala Pro Glu Ile Thr Lys Asp Gly Tyr Lys Val Ile Lys Ser
1               5                   10                  15

Ile Lys Pro Glu Asp
            20

<210> SEQ ID NO 7
<211> LENGTH: 22
<212> TYPE: PRT
<213> ORGANISM: Ehrlichia muris

<400> SEQUENCE: 7

Ser Lys Gly Phe Lys Glu Leu Asp Val Glu Lys Thr Asp Gly Met Gln
1               5                   10                  15

Phe Asp Arg Gly Tyr Leu
            20

<210> SEQ ID NO 8
<211> LENGTH: 24
<212> TYPE: PRT
<213> ORGANISM: Ehrlichia muris

<400> SEQUENCE: 8

Ser Glu Val Glu Val Lys Glu Arg Lys Asp Arg Val Glu Asp Ala Leu
1               5                   10                  15

His Ala Thr Arg Ala Ala Val Glu
            20
```